United States Patent [19]

Fischer

[11] Patent Number: 4,848,140
[45] Date of Patent: Jul. 18, 1989

[54] GUIDE DEVICE FOR A TEST BODY OF A HARDNESS MEASURING INSTRUMENT

[76] Inventor: Helmut Fischer, 6 Industriestrasse 20, 7032 Sindelfingen, Fed. Rep. of Germany

[21] Appl. No.: 192,664

[22] Filed: May 11, 1988

[30] Foreign Application Priority Data

Nov. 5, 1987 [DE] Fed. Rep. of Germany ....... 3737461

[51] Int. Cl.⁴ .............................................. G01N 3/48
[52] U.S. Cl. ...................................................... 73/81
[58] Field of Search ...................... 73/79, 81, 82, 818, 73/823, 150 R; 118/712; 427/8, 9; 310/14, 13

[56] References Cited

U.S. PATENT DOCUMENTS

| | | | |
|---|---|---|---|
| 3,202,886 | 8/1965 | Kramer | 310/14 |
| 3,425,263 | 2/1969 | Elliotte et al. | 73/79 |
| 4,094,188 | 6/1978 | Bellouin et al. | 73/81 |
| 4,111,039 | 9/1978 | Yamawaki et al. | 73/81 |
| 4,542,311 | 9/1985 | Newman et al. | 310/13 |
| 4,611,487 | 9/1986 | Krenn et al. | 73/81 |
| 4,671,104 | 6/1987 | Fischer | 73/81 |
| 4,691,559 | 9/1987 | Fischer | 73/81 |

FOREIGN PATENT DOCUMENTS

| | | | |
|---|---|---|---|
| 0603531 | 10/1934 | Fed. Rep. of Germany | 73/81 |
| 0676908 | 8/1979 | U.S.S.R. | 73/81 |
| 1040382 | 9/1983 | U.S.S.R. | 73/81 |

Primary Examiner—Stewart J. Levy
Assistant Examiner—Robert R. Raevis

[57] ABSTRACT

A device for guiding a hardness test body has a first bar device supporting the test body on one end, the geometric central axis of the bar device passing through the middle of the test body, and a second bar device which is substantially perpendicular to the first bar device. The second bar device comprises two flat broad leaf springs which are disposed parallel and at a considerable distance from each other with the light direction in the geometric central axis. A rigid bearing block of considerable height is immovable in the measuring position and extends parallel with the central axis. One end of the leaf springs is rigidly clamped on the bearing block. The other end of the leaf springs is rigidly connected to the first bar device which extends at least over the distance between the leaf springs. The effective length of the leaf springs is the same. A third bar device lies between the leaf springs and is pivotably mounted through the bearing block, with one end connected to the first bar device and compensating weights on the other end.

20 Claims, 5 Drawing Sheets

GUIDE DEVICE FOR A TEST BODY OF A HARDNESS MEASURING INSTRUMENT

This invention relates to a device for guiding a test body of a hardness measuring instrument.

BACKGROUND OF THE INVENTION AND RELEVANT PRIOR ART

Such a device is known from German published specification No. P 3408554.8 (U.S. Pat. No. 4,671,104, and U.S. Pat. No. 4,691,559, English Pat. No. 2155639, Japanese published specification No. 75655/84). According to U.S. Pat. No. 4,691,559 FIG. 1 thereof, a test body 67 is provided from which a first bar device emerges vertically upwardly and merges into a second horizontal bar device 37. Here, the geometric central axis 21 is important. The second bar device 37 is mounted on a bearing device in the form of the rotor of a rotary magnet device 31. The disadvantages of this arrangement are as follows:

(a) There is friction in the bearing of the rotary magnet.

(b) It is true that the second bar device 37 is comparatively long, although by virtue of problems with mass and the problem of usefulness as a hand-held appliance soon applies limits to the length; nevertheless, upon a rotation as indicated by the arrow 39, the direction of the first bar device changes in relation to the geometric longitudinal axis 21, so that that side of the test body 67 which is closer to the rotary magnet 31 is pressed in that direction. However, the first bar device ought to remain in the geometric central axis 21 or only undergo a parallel translatory displacement, and then only by an amount which can be disregarded from the point of view of measurement technique.

(c) Measurement of hardness can be described as a method which derives results from finding out how a material behaves when subject to the action of force. By reason of the aforesaid properties, however, it is not with the prior art device possible to this degree to record the depth profile of the hardness. The hardness is particularly of interest right in the vicinity of the surface and to this end, the prior art device is not sensitive enough.

Devices of the relevant prior art include the following features:

A first bar device having an end portion and a geometric central axis.

A test body supported on the end portion, the geometric central axis of the first bar device passing through the middle of the test body.

A bearing device.

And, a second bar device substantially perpendicular to the first bar device, having one end portion rigidly connected to the first bar device and another end portion fixed in the longitudinal direction of the second bar device in such a way as to be immovable on the bearing device, the bearing device being immovable in the longitudinal direction of the second bar device.

OBJECT AND STATEMENT OF THE INVENTION

The object of the invention is to provide a device which can still be constructed to the size of a hand-held instrument but which avoids the aforementioned drawbacks.

According to the invention, this object is achieved by the following features:

(a) The bearing device is a rigid bearing block of considerable height, which is immovable when the device is in the measuring position and which extends parallel to the geometric central axis of the first bar device, (b) The second bar device comprises two flat broad-leaf springs that are disposed parallel with and at a considerable distance from each other, having a light direction in said geometric central axis, (c) The broad-leaf springs have one end zone rigidly clamped on the bearing block, (d) The broad-leaf springs have another end zone rigidly connected to the first bar device, and the first bar device extends at least over the distance between the broad-leaf springs, and (e) The effective lengths of the broad-leaf springs are the same.

Such an embodiment eliminates friction. The geometric central axis of the test body always remains parallel with the geometric central axis of the first bar device. The lateral offset between the moment of application to the surface of the material to be tested up to the highest stepwise applied force is in practice less than 1 nanometer and can thus be disregarded. The system is ideal insofar as without any naturally required damping, it is for practical purposes undamped in itself, which can be seen in that it undergoes secondary vibration for quite some time after impact. A reproducibility of 0.1 milli-Newtons to 1 Newton can be achieved. Leaf springs of the order of 1 cm width are in the heavy direction so rigid that the first bar device remains laterally unmoved, so that the test body penetrates the surface at a right-angle even with inhomogenous material, and does not slip off sideways.

The following additional features are described in a preferred embodiment.

The broad-leaf springs have a position of rest in which they are free from tension. This makes it possible to avoid the "frog clicker" effect which can happen with leaf springs. For instance, this would be the case if the leaf springs were to be stamped out, because then at least one stamping burr would occur somewhere or another. The leaf springs must be absolutely flat and have homogeneous properties over their entire width. Even when they are cut with shears or a guillotine, the cut edges would lead to inhomogenous properties. However, it is not necessary for the leaf springs to be orientated according to the direction of the fibers in the microstructure.

The broad-leaf springs have a peripheral form that is etched. These leaf springs represent a particularly ideal solution to the above demands. In that case, it is not the surface but only the peripheral edges of the leaf springs which is etched.

The broad-leaf springs continue flat in the bearing block, the bearing block has clamping jaws that clamp fast to the broad-leaf springs and act at right-angles to the plane of the broad-leaf springs and complementary abutments into which the broad-leaf springs fit, and the broad-leaf springs have transitions between a clamping zone and a free zone that with respect to each other are parallel with the geometric central axis. The clamping locations are ideal, there being no need for the leaf springs to be soldered or spot welded, which would cause them to be stressed. A clamping effect which is stree-free in this direction is achieved, the parallelism for the first bar device being retained for any amount of deflection.

The broad-leaf springs are hardened from type V2A steel. This provides leaf springs which offer the necessary resilience properties but which do not corrode or alter in any other way. Since the leaf springs, because they are thin, have a relatively large surface area, environmental conditions would in course of time change the properties of the leaf springs.

The broad-leaf springs are composed of beryllium-copper. These leaf springs are insensitive to electrical and magnetic fields and are therefore oustandingly suitable because someone making a measurement often has no idea whether the measurement is being performed in an electrical and/or magnetic field.

The broad-leaf springs are in the region of 7 to 21 mm wide and have a thickness in the range of tenths of a millimeter. This results in devices having dimensions that make them usable as a hand-held instrument while they nevertheless work with a high level of accuracy.

The width of the broad-leaf springs is 12 mm plus/-minus 20% and the thickness is 0.1 mm+100% to 50%. This produces in the lateral direction virtually rigid leaf springs but which nevertheless in their light direction are bendable without excessively powerful forces having to be applied.

The broad-leaf springs have an effective length of 4 to 7 times their width. As a result, the leaf springs likewise remain stress-free in this area, while the area of the first bar device remains however lightweight and also rigid.

The other end zone of the broad-leaf springs have tension-free recesses and a hollow tube is held in tension-free manner in one of the recesses, extends coaxially with the geometric longitudinal axis of the first bar device and is very light and very rigid. As a result, the small tube may remain straight. Bending it would influence its properties or alternatively it would have to be made more solid.

A coaxial mount for a coaxial carrier of the test body is provided at the end portion of the first bar device. This means that the force can be exerted on the bar device. This direct application of force is substantially more favorable than an indirect application, for example through further bar devices or to the leaf springs.

The first bar has another end portion and a force generating device is provided and engages this other end portion of the first bar device. This means that a measuring instrument with the device according to the invention can be used in any position, since the device according to the invention always occupies the same starting position regardless of the position in space and without actuating the force-generating device.

Substantially in a middle zone between the broad-leaf springs there is a third bar device which, when in the position of rest, extends parallel to the broad-leaf springs and has one end portion connected to the first bar device, a middle portion pivotally mounted in the bearing block and another end portion, and a counterweight is carried by the other end portion of the third bar device which compensates for movable mass on the other side of the middle portion. This means that the system has less mass. It is able wonderfully to support the counterweight and coupling the third bar device to the first bar device (small tube) is optimum.

The third bar device comprises a small, rigid, lightweight tube, having one end with a short, soft spring thereon connected to the first bar device. The short, soft spring is a leaf spring parallel with the two broad-leaf springs and has a deep-waisted portion. By virtue of these features, the type of spring also used with other leaf springs can be employed, a hinge-like connection being obtained which is, however, friction-free.

The pivotal mount for the third bar device is a leaf spring device, having a plane, which when in a position of rest is at right-angles to the longitudinal axis of the third bar device and which has a U-shaped centrally symmetrical recess with a resultant middle tongue and two lateral webs on either side thereof, the third bar device transverses the resultant middle tongue, and the two lateral webs have end portions clamped into the bearing block. This means that the pivotal mount is also friction-free and has such a configuration that the effects of the leaf springs are not lost and that the parallelism, the reproducibility and the wide range of measurement are all retained.

The two lateral webs are, while suspended, clamped in said bearing block, and the U-shape has inner lugs pointing upwards. These features counteract the fact that the device is mostly used with the test body oriented downwards.

A stand and clamping means are provided, and the bearing block is mounted rigidly on the stand and can be moved up and down according to height when the clamping means have been slackened. This means that the bearing block remains adjustable and nevertheless, while in use, is rigidly located relative to a housing of the instrument in which the device is used.

The hollow tube comprises a coaxial per se known probe, and means define a hole through which the probe projects into the tube and a measuring pole is provided for the probe. By virtue of these features, the coaxiality conditions are largely improved and the interior of the tube is used for a protected position of the probe as well as of the measuring pole.

The measuring pole is made from ferrite.

An aperiodic damping means is provided.

DESCRIPTION OF THE DRAWINGS

The invention will now be explained with reference to a preferred embodiment shown in the accompanying drawings, in which.

DESCRIPTION OF A PREFERRED EMBODIMENT

Figure 1:
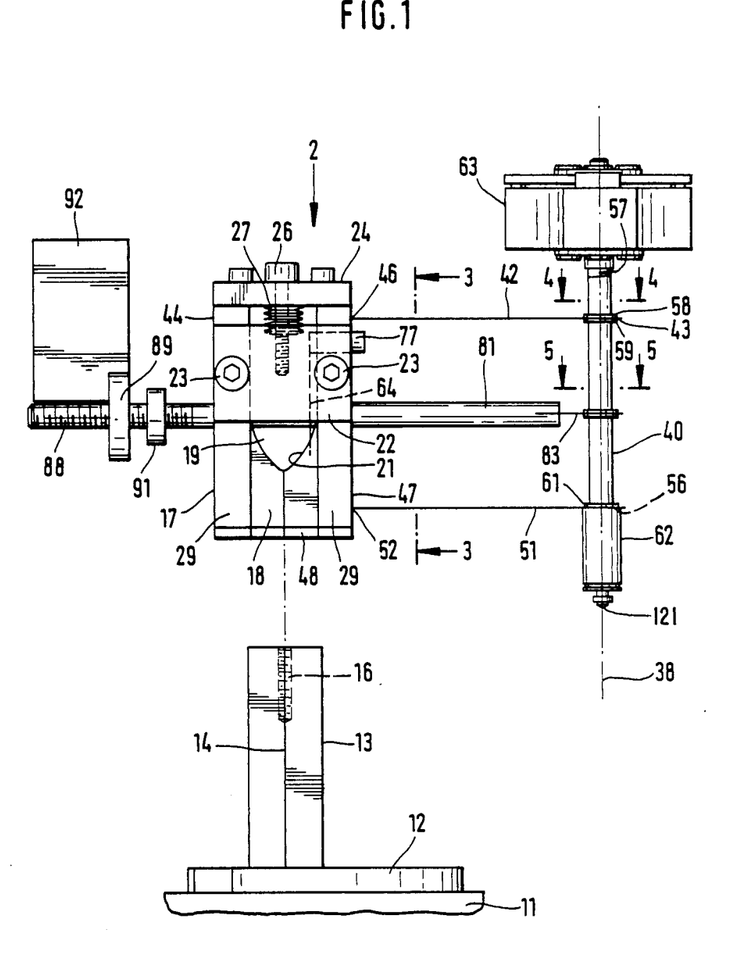
FIG. 1 is a partially exploded side view of the device according to the invention.
Figure 2:
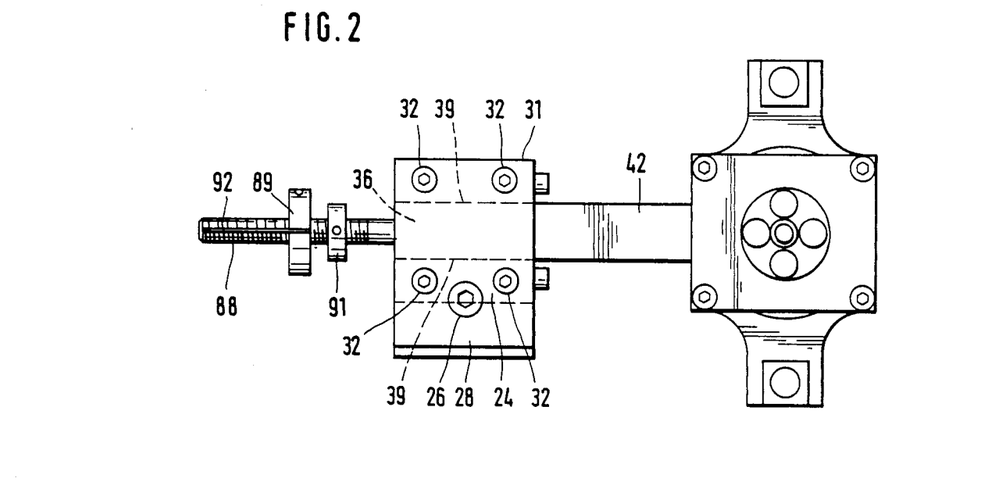
FIG. 2 is a view according to the arrow 2 in FIG. 1.
Figure 3:
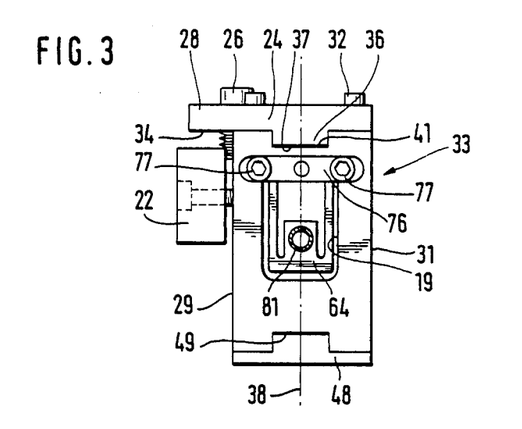
FIG. 3 is a section taken on the line 3—3 in FIG. 1.
Figure 4:
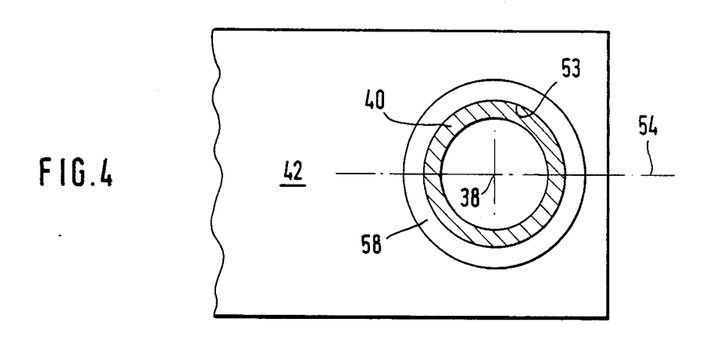
FIG. 4 is a section taken on the line 4—4 in FIG. 1.
Figure 9:
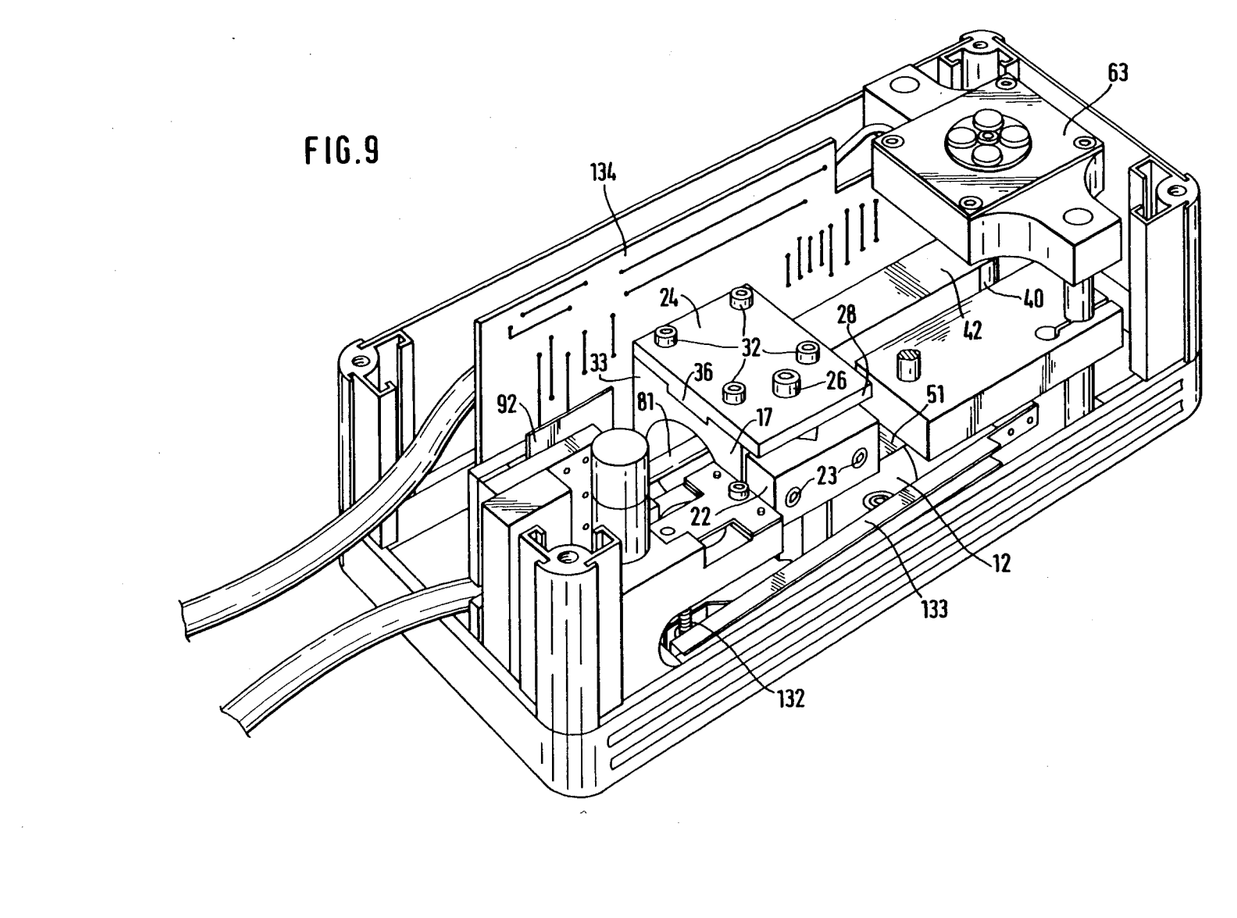
FIG. 9 is a perspective overall view of a hand-held instrument, partly opened.

Screwed onto the bottom 11 of a hardness measuring instrument shown in FIG. 9 is a carrier plate 12 on which a stand 13 is fixed which has a quadratic cross-section and of which one edge 14 is facing forwardly in FIG. 1. Extending within it from an end face is a blind screwthreaded hole 16. Corresponding to the square cross-section of the stand 13, a triangularly prismatic guide 18 is incorporated into a metallic bearing block 17 from the latter's front face and intersects a longitudinal recess 19 (FIG. 3), which is why the lines of intersection 21 are shown in FIG. 1. A clamping block 22 is secured by screws 23 to what is in FIG. 1 the front face of the bearing block 17 and has a recess matching the guide 18 so that the square cross-section of the stand 13 can be accommodated and almost completely enclosed when the screws 23 are tightened, the stand 13 being clamped securely so that it is no longer displaceable in the direction of its height. The bearing block 17 comprises an upper clamping plate 24 in which there is a through bore aligned with the blind threaded hole 16. Traversing this through bore is the threaded shank of a screw 26 which is screwed into the blind hole 16. Between the under side of the clamping plate 24 and the upper end face of the stand 13 there is clamped a set of spring washers 27. As the screws 23 are slackened, the bearing block 17 moves down the stand 13 or upwards if the screw 26 is turned in the other direction. For the set of plate springs 27 and the screw 26, the clamping plate 24 has a projection 28 pointing to the left in FIG. 3 and which extends beyond the flat surface 29 shown on the left in FIG. 3. Close to the surface 29 and the flat surface 31 on the bearing block 17 which is parallel with it, the clamping plate 24 has four through bores to receive four screws 32 which are screwed into a member 33 which, as shown in FIG. 3, is shaped like a compressed H and which forms the core of the bearing block 17. Extending over its flat under side 34 and always at a right-angle to a geometrical longitudinal axis 38 of a small tube 40 which will be discussed later, the clamping plate 24 has a projection 36. The lateral flanks 39 of the projection 36 extend parallel with one another and vertically in the view shown in FIG. 3. According to FIG. 3, complementary to this configuration, the member 33 has a broad flat groove 41 disposed centrally and also perpendicular to the geometric longitudinal axis 38. Between the under side 37 and the bottom of the groove 41 is clamped the (according to FIG. 1) left-hand portion of a first leaf spring 42 which consists of beryllium/copper. The full scale drawing in FIG. 1 shows the front end 43 of the leaf spring 42. The rear end 44 is aligned with the back of the bearing block 17, producing a clamping area about 3 cm long which is very long in comparison with the overall length of the leaf spring 42 which is 88.5 mm. The emergence 46 of the leaf spring 42 from the bearing block 17 lies clearly in the flat side 47 which is on the right in FIG. 1 and which extends perpendicular with the geometric longitudinal axis 38. At the emergence 48 (sic!), the projection 36 and the bottom of the groove 41 are sharply edged so that there is a clearly defined emergence 46, a clearly defined clamping effect and a clearly defined gap in respect of the geometric longitudinal axis 38. The leaf spring 42 is 0.1 mm thick, which is why it cannot be seen in the view in FIG. 3 which is likewise a full-scale drawing. It is 12 mm wide and the groove 41 is only a little wider so that it can accommodate the leaf spring 42 without any clamping. As FIG. 3 shows, the under side 37 and the bottom of the groove 41 are at right-angles to the geometric longitudinal axis 38.

Screwed to the under side of the body 33 is a clamping plate 48 which, except for the projection 28, is identical to but somewhat thinner than the clamping plate 24. By means of it and the groove 49 directed in opposition to the groove 41, an identical second leaf spring 51 is secured. Since the circumstances have been accurately described with reference to the leaf spring 42, they need not be repeated here. It should merely be pointed out that also this groove 49 must extend at right-angles to the geometrical longitudinal axis 38 and that the point of emergence 52 is at the same distance from the geometric longitudinal axis 38. Also the leaf spring 51 is of Cu Be 2 and is 0.1 mm thick. The other dimensions are also completely identical. The leaf springs 42, 51 are absolutely flat and have no inherent tension which might originate from unsuitable machining processes or from any bulges in them. The homogeneity of the properties is also assured in respect of forces of 0.1 to 0.01 milli-Newtons.

Figure 5:
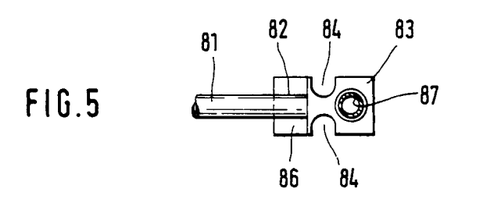
FIG. 5 is a section taken on the line 5—5 in FIG. 1.
Figure 6:
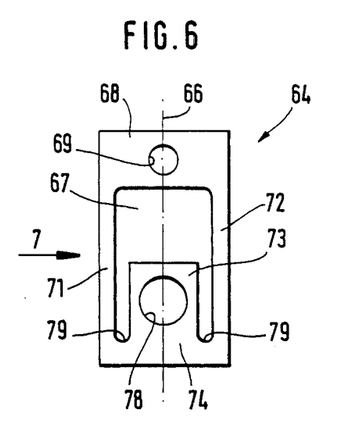
FIG. 6 is a view of a leaf spring serving a pivot joint.
Figure 7:
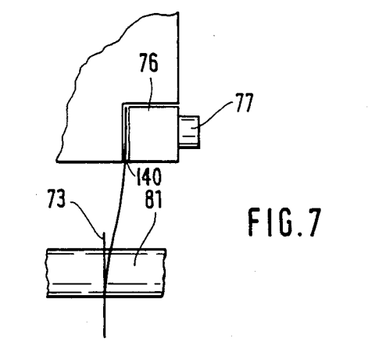
FIG. 7 is a view according to the arrow 7 in FIG. 6, partly broken away to illustrate the action of the leaf spring in FIG. 6.

In its free end zone, the leaf spring has a circular hole 53 6 mm in diameter. This, too, has been produced without stress at the edges, by etching. The hole 53 is both coaxial with the geometric longitudinal axis 38 and also exactly in the median line 54 of the leaf spring 42. By reason of this latter, there is no tendency to tilt. The leaf spring 51 comprises a hole 56 having exactly the same geometry. The small tube 40 consists of a titanium-/aluminium alloy so that it is both light and also rigid. It is produced by being cut from the solid. Its outside diameter corresponds to the diameter of the holes 53, 56. In the position of rest (neutral position), the small tube 40 is exactly coaxial with the geometric longitudinal axis 38. At the top, it has an external screwthread 57. The tube 40 is fitted into the hole 53 both by a small ring 58 being pushed on from above and also by a small ring 59 pushed on from the bottom. These separate rings are fastened to the tube 40 by a cold-setting glue. In the lower portion, at the height of the top of the leaf spring 51, the tube 40 has a circularly cylindrical shoulder 61, the under side of which is spaced apart from the right-hand end portion of the leaf spring 51 by exactly the same amount as the gap between the points of emergence 46 and 52. Under the shoulder 61, the tube 40 traverses the hole 56 and projects a little farther downwards so that it fits into a coaxial sleeve 62. To the upper portion of this sleeve 62 and the shoulder 61, a little cold setting adhesive has been applied. "Cold" in this case naturally means a temperature which does not alter the structure of the leaf springs. Right at the bottom, the sleeve 62 grips a diamond 128 which constitutes the test body and screwed onto the external screwthread 57 is a coaxially arranged electric motor drive unit 63. This configuration would be adequate if one were sure that the geometric longitudinal axis 38 would always point to the centre of the earth during measurement. However, in order to be able to measure in any desired position, further measures are adopted: a leaf spring 64 is shown in FIG. 6 to a scale of 2:1. It is 14 mm wide, 25 mm high, is likewise made from Cu Be 2, is 0.1 mm thick and is given its shape by etching, without stress. It is completely flat when at rest. Its median plane 66 is also simultaneously in the geometric longitudinal axis 38 and the median line 54. It is symmetrical with the median plane 66. Its plane which is in the plane of the drawing in FIG. 6 is parallel with the geometric longitudinal axis 38. The (in plan view) rectangular leaf spring 64 has in it a centrally symmetrical cut-out 67 of an upside-down U-shape. Above this is a broad clamping zone 68 with a positioning hole 69 from which two narrow arms 71, 72 extend downwardly on either side. Separated from these by the longitudinal arms of the U is a central tongue 73 which merges at the bottom and via a cross web 74, into the arms 71, 72. Where the corners of the cut-out 67 may during operation be exposed to stress, a radius of 0.75 mm is provided. The leaf spring 64 is clamped in the longitudinal cut-out 140 by a clamping plate 76 in stress and curvature-free manner so that it hangs in a vertical direction, the clamping force being applied by two screws 77. The positioning hole 69 is traversed by a positioning stud which is rigidly connected to the member 33. As FIG. 6 shows, the boundary edges of the leaf spring 64—in so far as they extend vertically—run parallel with the geometric longitudinal axis 38 or at right-angles to the latter if they extend horizontally. Etched centrally into the central tongue 73 is a circular hole 78, the central axis of which intersects the geometric longitudinal axis 38. The radii 79 are substantially lower down than the bottom edge of the hole 78 and are at least 2 mm away from the bottom edge so that the middle tongue 73 can, according to FIG. 7, when standing approximately vertically, move leftwards when a force at the hole 78 exerts a force directed leftwardly in FIG. 7. The arms 71, 72 then extend in a slight S-shape. This force can be applied by a second tube 81 which passes through the hole 78 being fixed rigidly therein by the above-mentioned adhesion technique. For reasons of weight and rigidity, the tube is likewise made from an aluminium-titanium alloy and is thin-walled. Its outside diameter is 5 mm and it is about 11.5 cm long. Its end portion which is on the right in FIG. 1 has a short transverse slot 82 which lies exactly in the plane of the leaf springs 42, 51, which means at a right-angle to the geometric longitudinal axis 38. A leaf spring 83 which is short in comparison with the leaf springs 42, 51 but is just as wide and consists of the same materials, and which is stress free in the position of rest and which has been etched in its contours has, as shown in FIG. 5, two deep lateral depressions 84 between which remains roughly one-quarter of the width of the leaf spring. To the left of this there remains a fin 86 which is glued without stress into the slot 82. As FIG. 1 shows, the right-hand end of the tube 81 is at a slight distance of about 8 mm from the geometric longitudinal axis 38. The leaf spring 83 is exactly at right-angles to the geometric longitudinal axis 38 and has a hole 87 corresponding to and completely flush with the holes 53, 56. By means of the same technique of small rings or mating flange in one piece with the tube 40, adhesive fixing is carried out in the peripheral zone of the hole 87.

The tube 81 has on the left and external screwthread 88 onto which is screwed a counterweight 89 with a locking nut 91. Furthermore, there is on the external screwthread 88 a disc 92 for an aperiodic electric damping device, the functioning of which is of no interest here. The counterweight 89 can be used to achieve such a fine equalisation of weights that with the configuration shown in FIG. 1 there is no flexion of the leaf springs 42, 51, 83.

Figure 8:
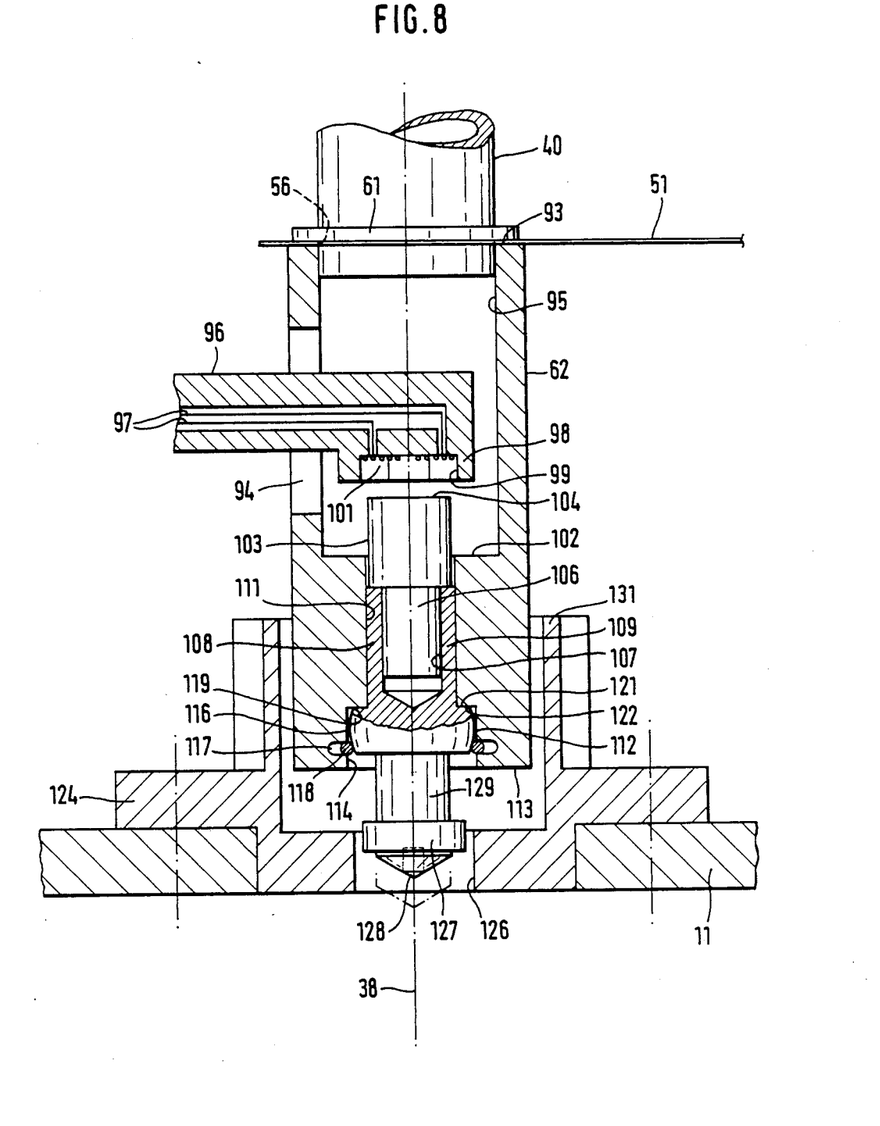
FIG. 8 is a section through the right-hand bottom part of the tube shown on the right in FIG. 1.

According to FIG. 8, which of course is shown to a scale of 10:1, we see at the top the tube 40 which is of 6 mm diameter. The sleeve 62 is secured by cold setting adhesive, in this sequence: collar 61 against the under side of which bears the leaf spring 51, the upper coaxial circularly cylindrical end face 93 of the aluminium sleeve 62 and the overlapping insertion of the very bottom portion of the tube 40 into an upper coaxial bore 95 of a farther downwardly extending stepped bore. According to FIG. 8, from the left, and according to FIG. 1, from the right, the sleeve 62 has in the remaining wall a large hole 94 into which projects an arm 96 rigid with the housing and in which there are electrical supply conductors 97 which lead to a probe head 98 which is comparable with the probe 77 in the U.S. Pat. No. 4,671,104, column 55 line 60 mentioned at the outset. In the coil space 99 coaxial with the geometric longitudinal axis 38 there is, as indicated, a coil 101. The bottom 102 of the bore 95 is considerably lower down than the bottom of the coil 101. Projecting upwardly from it is a measuring terminal 103 which consists of Al Cu Mg Pb F 38. Its end face 104 is finely finished and is at a right-angle to the geometric longitudinal axis 38. Its stud 106 fits securely in a bore 107 in a rotationally symmetrical diamond carrier 108. Its sleeve 109 fits in a coaxial continuation bore 111 which is not touched by the head of the measuring terminal 103. In the region below the end of the bore 107, the diamond carrier 108 has a convex bead 112 which projects outwardly. The bead 112 fits in a flat circularly cylindrical bore 114 which ends at the bottom end face 113 of the sleeve 62. The bore 114 has in its wall below the thickest point 116 of the bead 112 an inner peripheral groove 117 which extends at a right-angle to the geometric longitudinal axis 38 and in which there fits a snap ring 118 which in its position closer to the relaxed position projects at least partially into the bore 114 while in its completely relaxed position it does not project any farther therein than that corner 119 formed by the periphery of the bead 112 and a circular shoulder 121 which is at right-angles to the geometric longitudinal axis 38 and which forms on the inside the transition with the peripheral surface of the sleeve 109. This shoulder 121 lies on the bottom 122 of the bore 114, in fact in clearly defined fashion, being also securely held in this position by the snap ring 118 which is subject to tension and which—since it is slipped over the thickest point 116—seeks to push the bead 112 upwardly and with it the entire diamond carrier 108.

Disposed in the housing bottom 11 and shown in FIG. 8 is the insert 124 which comprises a central bore 126 through which the mount 127 of a diamond 128 can pass. Via a cylinder 129, the mount 127 is in one piece with the bead 112. The insert 124 also has a pot-shaped part 131 which is open at the top, prevents movements in an undesired direction and so protects the bottom part of the sleeve 62 and the diamond carrier 108. This construction makes it possible to measure coaxially in the immediate vicinity of the diamond 128 and permits of a very simple but reproducible interchangeability of the diamond carrier 108. The movement of end face 104 relative to probe head 98 follows almost directly (for practical purposes absolutely directly) the movement of the diamond 128 and of its tip. The end face 104 corresponds to the downwardly facing surface of the part 74 mentioned in the German published specification already mentioned at the outset.

FIG. 9 shows the disposition of the device according to the invention. The spindle 132 and the leaf spring 133 correspond to the spinde 104 and the leaf spring 96 in the German published specification. Any necessary electronics are mounted on a circuit board 134.

If the measuring terminal 103 is of aluminium, then from the point of view of forces, there is no retroaction between it and the coil 101. However, if it is as preferred produced entirely or at least in its upper part from ferrite, then there is a substantially better sensitivity of the indication. No retroaction could be measured with ferrite, either.

The centre of gravity of all masses acting on the tube 81, including its own mass, lies in the hole 78.

What is claimed is:

1. Device for guiding a test body of a hardness measuring instrument comprising:
   a first bar device having an end portion and a geometric central axis,
   a test body supported on said end portion, said geometric central axis of said first bar device passing through the middle of said test body,
   a bearing device,
   a second bar device substantially perpendicular to said first bar device, having one end portion rigidly connected to said first bar device and another end portion fixed in the longitudinal direction of said second bar device in such a way as to be immovable on said bearing device, said bearing device being immovable in the longitudinal direction of said second bar device,
   and the improvement wherein
   (a) said bearing device is a rigid bearing block of considerable height, which is immovable when in the measuring position and which extends parallel to said goemetric central axis of said first bar device,
   (b) said second bar device comprises two flat broad-leaf springs that are disposed parallel with and at a considerable distance from each other, having a light direction in said geometric central axis,
   (c) said broad-leaf springs each have one end zone rigidly clamped on said bearing block,
   (d) said broad-leaf springs each have another end zone rigidly connected to said first bar device, and said first bar device extends at least over the distance between said broad-leaf springs,
   (e) the effective lengths of said broad-leaf springs are the same,
   (f) a third bar device is substantially in a middle zone between said broad-leaf springs, and said third bar device when in a position of rest, extends parallel to said broad-leaf springs,
   (g) said third bar device has a first end portion connected to said first bar device, a middle portion pivotally mounted in said bearing block and a second end portion, and
   (h) said first end portion of said third bar device has a short soft spring thereon connected to said first bar device, and said second end portion of said third bar device carries a counterweight that compensates for movable mass on the other side of said middle portion.

2. Device according to claim 1, wherein said broad-leaf springs have a position of rest in which they are free from tension.

3. Device according to claim 2, wherein said broad-leaf springs have a peripheral form that is etched.

4. Device according to claim 1, wherein said broad-leaf springs lie flat when entering said bearing block, said bearing block has first clamping means that clamp fast said broad-leaf springs, and act at right-angles to the plane of said broad-leaf springs and complementary abutments into which said broad-leaf springs fit, and said broad-leaf springs have transitions between a clamping zone and a free zone that with respect to each other are parallel with said geometric central axis.

5. Device according to claim 1, wherein said broad-leaf springs are hardened from type V2A steel.

6. Device according to claim 1, wherein said broad-leaf springs are composed of beryllium-copper.

7. Device according to claim 1, wherein said broad-leaf springs are in the region of 7 to 21 mm wide and have a thickness in the range of tenths of a millimeter.

8. Device according to claim 7, wherein said width of the broad-leaf springs is 12 mm plus/minus 20% and said thickness is 0.1 mm + 100% to 50%.

9. Device according to claim 1, wherein said broad-leaf springs have an effective length of 4 to 7 times their width.

10. Device according to claim 1, wherein said other end zone of said broad-leaf springs have tension-free recesses, and said first bar device comprises a hollow tube held in tension-free manner in one of said recesses, which extends coaxially with said geometric longitudinal axis and is very light and very rigid.

11. Device according to claim 10, wherein in said hollow tube comprises a coaxial per se known probe, and further comprising means defining a hole through which said probe projects into said tube and a measuring pole for said probe.

12. Device according to claim 11, wherein said measuring pole is made from ferrite.

13. Device according to claim 1, wherein a coaxial mount for a coaxial carrier of said test body is provided at said end portion of said first bar device.

14. Device according to claim 1, wherein said first bar has another end portion and a force generating device is provided and engages said other end portion of said first bar device.

15. Device according to claim 1 wherein said third bar device comprises a small, rigid, lightweight tube.

16. Device according to claim 15, wherein said short, soft spring is a leaf spring parallel with said two broad-leaf springs and has a deep-waisted portion.

17. Device according to claim 1 wherein said pivotal mount for said third bar device is a leaf spring device, having a plane, which when in a position of rest is at right-angles to the longitudinal axis of said third bar device and which has a U-shaped centrally symmetrical recess with a resultant middle tongue and two lateral webs on either side thereof, said third bar device transverses said resultant middle tongue, and said two lateral webs have end portions clamped into said bearing block.

18. Device according to claim 17, wherein said two lateral webs are, while suspended, clamped in said bearing block.

19. Device according to claim 1, wherein a stand and second clamping means are provided, and said bearing block is mounted rigidly on said stand and can be moved up and down according to height when said second clamping means have been slackened.

20. Device according to claim 1, wherein an aperiodic damping means is provided.

* * * * *